United States Patent
Liu et al.

(10) Patent No.: US 10,926,108 B2
(45) Date of Patent: Feb. 23, 2021

(54) BEAM SHAPING ASSEMBLY FOR NEUTRON CAPTURE THERAPY

(71) Applicant: NEUBORON MEDTECH LTD., Jiangsu (CN)

(72) Inventors: Yuanhao Liu, Jiangsu (CN); Weilin Chen, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 457 days.

(21) Appl. No.: 16/188,644

(22) Filed: Nov. 13, 2018

(65) Prior Publication Data

US 2019/0160307 A1    May 30, 2019

Related U.S. Application Data

(63) Continuation of application No. PCT/CN2017/092442, filed on Jul. 11, 2017.

(30) Foreign Application Priority Data

Oct. 28, 2016 (CN) .......................... 201610966285.3
Oct. 28, 2016 (CN) .......................... 201621187821.1

(51) Int. Cl.
*A61N 5/10* (2006.01)
*G21K 5/04* (2006.01)
(Continued)

(52) U.S. Cl.
CPC ......... *A61N 5/1042* (2013.01); *A61N 5/1077* (2013.01); *G21K 1/10* (2013.01);
(Continued)

(58) Field of Classification Search
CPC ............................ A61N 5/1077–1084; A61N 2005/1085–1098; A61N 5/10–1084
See application file for complete search history.

(56) References Cited

U.S. PATENT DOCUMENTS

| 5,703,918 A | 12/1997 | Hiismaki et al. |
| 2016/0158579 A1* | 6/2016 | Liu ........................... G21G 4/02 600/1 |
| 2016/0220839 A1* | 8/2016 | Kuri ......................... H05H 6/00 |

FOREIGN PATENT DOCUMENTS

| CN | 101829409 A | 9/2010 |
| CN | 104548388 A | 4/2015 |

(Continued)

OTHER PUBLICATIONS

International Search Report of PCT/CN2017/092442, dated Sep. 6, 2017.

*Primary Examiner* — Thaddeus B Cox
(74) *Attorney, Agent, or Firm* — Locke Lord LLP; Tim Tingkang Xia, Esq.

(57) ABSTRACT

The present disclosure provides a beam shaping assembly for neutron capture therapy, wherein the beam shaping assembly includes a neutron generating device, a moderator, a disturbing unit and a beam outlet. The neutron generating device is used to generate neutrons that form a neutron beam in a direction from the neutron generating device to the beam outlet, the moderator adjacent to the neutron generating device for adjusting fast neutrons in the neutron beam to epithermal neutrons. The disturbing unit is located between the moderator and the beam outlet for passing through the neutron beam and reducing the gamma ray content in the neutron beam passing through the beam outlet. The technical solution provided by the present disclosure can effectively reduce the gamma ray content in the neutron beam under the premise that the quality of the neutron beam is not significantly adversely affected.

18 Claims, 2 Drawing Sheets

(51) Int. Cl.
*G21K 1/10* (2006.01)
*H05H 3/06* (2006.01)
*G21G 4/02* (2006.01)

(52) U.S. Cl.
CPC ............... *G21K 5/04* (2013.01); *H05H 3/06* (2013.01); *A61N 2005/109* (2013.01); *A61N 2005/1094* (2013.01); *A61N 2005/1098* (2013.01); *G21G 4/02* (2013.01); *G21K 2201/068* (2013.01)

(56) References Cited

FOREIGN PATENT DOCUMENTS

| | | |
|---|---|---|
| EP | 3026673 A1 | 6/2016 |
| JP | 2007242422 A | 9/2007 |
| JP | 2008022920 A | 2/2008 |
| JP | 2009192488 A | 8/2009 |
| JP | 2014113215 A | 6/2014 |

\* cited by examiner

BEAM SHAPING ASSEMBLY FOR NEUTRON CAPTURE THERAPY

RELATED APPLICATION INFORMATION

This application is a continuation of International Application No. PCT/CN2017/092442, filed on Jul. 11, 2017, which claims priority to Chinese Patent Application No. 201610966285.3, filed on Oct. 28, 2016 and Chinese Patent Application No. 201621187821.1, filed on Oct. 28, 2016, the disclosures of which are hereby incorporated by reference.

FIELD OF THE DISCLOSURE

The present disclosure relates to a beam shaping assembly, and, more particularly, to a beam shaping assembly for neutron capture therapy.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}$B)-containing pharmaceuticals have high neutron capture cross section and produces $^4$He and $^7$Li heavy charged particles through $^{10}$B(n,$\alpha$)$^7$Li neutron capture and nuclear fission reaction. As illustrated in FIGS. 1 and 2, a schematic drawing of BNCT and a nuclear reaction formula of $^{10}$B (n, $\alpha$)$^7$Li neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

In the process of neutron capture therapy, the generation of neutrons and the changes of the neutron energy spectrum in the beam shaping assembly tend to produce a large number of gamma rays. The gamma rays have a strong penetrating ability. When the human body is exposed to the gamma rays, the gamma rays can enter the interior of the body and ionize with cells of the body. Ionization-generated ions can erode complex organic molecules, such as proteins, nucleic acids and enzymes, which are the main components constituting the living cell tissues. Once they are destroyed, it can cause normal chemical processes in the human body to be disturbed, even cause the death of cells in severe cases.

It has not been found in the prior art to change the beam shaping assembly to reduce the gamma ray content in the neutron beam under the premise that the neutron beam quality is not affected.

The statements in this section merely provide background information related to the present disclosure and may not constitute prior art.

SUMMARY

In order to reduce the gamma ray content in the neutron beam during neutron capture therapy, one aspect of the present disclosure provides a beam shaping assembly for neutron capture therapy, the beam shaping assembly includes a neutron generating device, a moderator, a disturbing unit and a beam outlet. The neutron generating device is housed within the beam shaping assembly for generating neutrons that form a neutron beam in a direction from the neutron generating device to the beam outlet, the neutron beam defines a beam axis. The moderator is adjacent to the neutron generating device for moderating fast neutrons in the neutron beam to epithermal neutrons. Wherein the beam shaping assembly produces gamma rays in the process of adjusting the neutron beam energy spectrum, the disturbing unit is located between the moderator and the beam outlet for passing through the neutron beam and reducing the gamma ray content in the neutron beam passing through the beam outlet.

Accordingly, the disturbing unit is located between the moderator and the beam outlet for passing the neutron beam therethrough and reducing the gamma ray content in the neutron beam passing through the disturbing unit under the premise of minimal influence on the neutron energy. The present disclosure uses the ratio of gamma rays in the neutron beam to the neutron beam flux to evaluate the effects of addition of the disturbing unit and using use of different materials of the disturbing units on the gamma rays. The present disclosure uses the advantage depth, the advantage dose rate, and the 30 RBE-Gy treatable depth in the phantom beam quality to evaluate the effects of addition of the disturbing unit and use different materials of the disturbing units on the neutron beam.

The effect of the disturbing unit on the absorption and reflection of the gamma rays is also related to the material constituting the disturbing unit.

Preferably, in the beam shaping assembly for neutron capture therapy, the material of the disturbing unit is selected from the group consisting of rhenium, hafnium, lutetium, lead, cerium, zinc, bismuth, terbium, indium, antimony, gallium, lanthanum, tellurium, tin, selenium, yttrium, aluminum, strontium, barium, silicon, zirconium, rubidium, calcium, sulfur, iron, carbon, beryllium, magnesium, phosphorus, chromium, lithium, sodium, nickel element and combinations thereof.

Furthermore, in the beam shaping assembly for neutron capture therapy, the internal structure of the disturbing unit is a dense structure or a porous structure.

The porous structure is called relative to the dense structure, which means that the interior of the disturbing unit is not tight and compact, and the solid material that constitutes the disturbing unit is a complete whole with a plurality of pores inside thereof, for example, a honeycomb structure or an internal hollow structure. The density of the porous structure is less than the density of the dense structure.

Further, in the beam shaping assembly for neutron capture therapy, the disturbing unit is a cylinder and the axis of the cylinder coincides or is parallel to the beam axis. The size of the cylinder is preferably such that the radius of the bottom surface of the cylinder is 5 to 6 cm, and the height of the cylinder is 3 to 5 cm. In a preferred embodiment, the disturbing unit having such size and shape is placed in a beam shaping assembly with a height of 80 to 100 cm and a radius of the bottom surface of 60 to 70 cm, and significantly reduces the gamma ray content by comparison with the beam shaping assembly to which the disturbing unit is not added. Certainly, it is well known to those skilled in the art that placing the disturbing unit in the beam shaping assembly with other shapes or sizes also significantly reduces the gamma ray content, as will be detailed below.

Preferably, in the beam shaping assembly for neutron capture therapy, the moderator and the disturbing unit are externally surrounded by a reflector. The reflector is used for reflecting the neutrons deviating from the neutron beam back to the neutron beam to enhance the neutron beam intensity. The reflector is made of a material having a strong neutron reflection ability, preferably at least one of lead or nickel. When the gamma rays encounters a substance, there is a photoelectric effect, a Compton effect, and an electron pair effect, which cause a certain degree of attenuation. When gamma rays in a neutron beam encounter the disturbing unit, the disturbing unit reduces the gamma ray content in the neutron beam by absorbing gamma rays through photoelectric effect, scattering gamma rays through Compton effect, or converting gamma rays into positive and negative electron pairs through electron pair effect, respectively, and the gamma rays scattered by the disturbing unit is further attenuated by reabsorption or reflection after encountering the reflector.

Preferably, in the beam shaping assembly for neutron capture therapy, when the disturbing unit is made of any single element of rhenium, hafnium, lutetium, lead, cerium, zinc, bismuth, terbium, indium or antimony, the proportion of gamma rays in the neutron beam is reduced by at least 30%, which means that the ratio of gamma rays in the neutron beam to the neutron beam flux is reduced by at least 30%. It can be seen that the above element can effectively reduce the gamma ray content in the neutron beam when it is used as a disturbing unit.

Further, in the beam shaping assembly for neutron capture therapy, when the material of the disturbing unit is selected from the group consisting of rhenium, hafnium, lutetium, lead, cerium, zinc, bismuth, terbium, indium, antimony, gallium, lanthanum, tellurium, tin, selenium, yttrium, aluminum, strontium, barium, silicon, zirconium, rubidium, calcium, sulfur, iron, carbon, beryllium, magnesium, phosphorus, chromium, lithium, sodium, nickel element and combinations thereof, in the phantom beam quality of the neutron beam passing through the disturbing unit, the advantage depth is ≥10.69 cm, the advantage dose rate is ≥5.54, and the 30 RBE-Gy treatable depth is ≥6.77 cm.

Neutron beam quality plays a crucial role in the treatment effect during the process of neutron capture therapy. Another aspect of the present disclosure is to reduce the gamma ray content in the neutron beam under the premise that the quality of the neutron beam is not significantly adversely affected. When the advantage depth is greater than or equal to 10 cm, the advantage dose rate is greater than or equal to 5.5, the 30 RBE-Gy treatable depth is greater than or equal to 6.5 cm, the therapeutic effect is good. Preferably, the advantage depth is ≥10.69 cm, and the advantage dose rate is ≥5.54, and the 30 RBE-Gy treatable depth is ≥6.77 cm.

In another aspect of the present disclosure provides a beam shaping assembly for neutron capture therapy, including: a neutron generating device housed within the beam shaping assembly for generating neutrons, wherein neutrons form a neutron beam in a direction from the neutron generating device to the beam outlet, the neutron beam defines a beam axis; a moderator adjacent to the neutron generating device for moderating fast neutrons in the neutron beam to epithermal neutrons; a reflector surrounding the moderator and the disturbing unit for reflecting the neutrons deviating from the neutron beam back to the neutron beam to enhance the neutron beam intensity; a disturbing unit; and a beam outlet; wherein the beam shaping assembly produces gamma rays in the process of adjusting the neutron beam energy spectrum, the disturbing unit is located after the neutron generating device for passing through the neutron beam and reducing the gamma ray content in the neutron beam passing through the beam outlet.

More particularly, the material of the disturbing unit is selected from the group consisting of rhenium, hafnium, lutetium, lead, cerium, zinc, bismuth, terbium, indium, antimony, gallium, lanthanum, tellurium, tin, selenium, yttrium, aluminum, strontium, barium, silicon, zirconium, rubidium, calcium, sulfur, iron, carbon, beryllium, magnesium, phosphorus, chromium, lithium, sodium, nickel element and combinations thereof.

More particularly, the internal structure of the disturbing unit is a dense structure or a porous structure.

More particularly, when the neutron beam containing gamma rays passes through the disturbing unit, the disturbing unit reduces the gamma ray content in the neutron beam by absorbing gamma rays through photoelectric effect, scattering gamma rays through Compton effect, or converting gamma rays into positive and negative electron pairs through electron pair effect, respectively, and the gamma rays scattered by the disturbing unit is further attenuated by reabsorption or reflection after encountering the reflector.

More particularly, the disturbing unit is a cylinder defining an axis and the axis of the cylinder coincides or is parallel to the beam axis.

In yet another aspect of the present disclosure provides a beam shaping assembly for neutron capture therapy, including: a neutron generating device housed within the beam shaping assembly for generating neutrons, wherein neutrons form a neutron beam in a direction from the neutron generating device to the beam outlet, the neutron beam defines a beam axis; a moderator adjacent to the neutron generating device for moderating fast neutrons in the neutron beam to epithermal neutrons; a disturbing unit; and a beam outlet; wherein the beam shaping assembly produces gamma rays in the process of adjusting the neutron beam energy spectrum, the disturbing unit defines an axis and the axis of the disturbing unit coincides or is parallel to the beam axis for passing through the neutron beam and reducing the gamma ray content in the neutron beam passing through the beam outlet, the internal structure of the disturbing unit is a porous structure.

More particularly, the material of the disturbing unit is selected from the group consisting of rhenium, hafnium, lutetium, lead, cerium, zinc, bismuth, terbium, indium, antimony, gallium, lanthanum, tellurium, tin, selenium, yttrium, aluminum, strontium, barium, silicon, zirconium, rubidium, calcium, sulfur, iron, carbon, beryllium, magnesium, phosphorus, chromium, lithium, sodium, nickel element and combinations thereof.

More particularly, the beam shaping assembly further includes a reflector surrounding the moderator and the disturbing unit for reflecting the neutrons deviating from the neutron beam back to the neutron beam to enhance the neutron beam intensity, and wherein the reflector is made of a material having a strong neutron reflection ability.

More particularly, when the neutron beam containing gamma rays passes through the disturbing unit, the disturbing unit reduces the gamma ray content in the neutron beam by absorbing gamma rays through photoelectric effect, scattering gamma rays through Compton effect, or converting gamma rays into positive and negative electron pairs through electron pair effect, respectively, and the gamma rays scattered by the disturbing unit is further attenuated by reabsorption or reflection after encountering the reflector.

More particularly, the disturbing unit is a cylinder, the radius of the bottom surface of the cylinder is 5 to 6 cm, and the height of the cylinder is 3 to 5 cm.

The shape, structure, and material of the disturbing unit mentioned in the present disclosure are not limited to those defined by the above preferred technical solutions, and any disturbing unit placed in the beam shaping assembly is within the scope of the present disclosure as long as it satisfies the ability to reduce the gamma ray content in the neutron beam without significantly adversely affecting the quality of the neutron beam.

Further areas of applicability will become apparent from the description provided herein. It should be understood that the description and specific examples are intended for purposes of illustration only and are not intended to limit the scope of the present disclosure.

DETAILED DESCRIPTION

Figure 1:
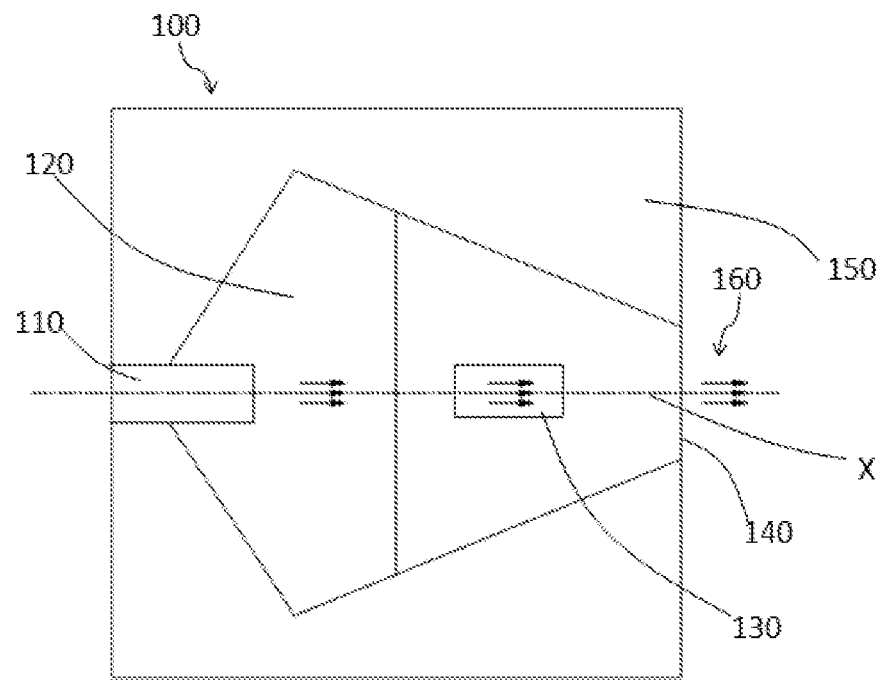
FIG. 1 is a schematic view of a beam shaping assembly with a diamond-shaped moderator.

The present disclosure will now be described in further detail with reference to the accompanying drawings in order to enable those skilled in the art to practice with reference to the specification.

The following description of the preferred embodiments is merely exemplary in nature and is in no way intended to limit the invention, its application, or uses.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n)$^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The ideal target should have these characteristics of high neutron yield, produced neutron energy distribution close to the epithermal neutron energy zone (described in detail below), no excessively strong radiation generation, safety, inexpensive, easy to operate, and high temperature resistance. However, it is practically impossible to find a nuclear reaction that meets all the requirements. A target made of lithium metal is used in the embodiments of the present disclosure. However, it is well known to those skilled in the art that the target can also be made of other metal materials other than the metal materials discussed above.

Regardless of whether the neutron source of the boron neutron capture therapy come from the nuclear reactor or the nuclear reaction of the charged particles accelerated by an accelerator and the target, a mixed radiation field is generated, i.e., the beam contains low-to-high energy neutrons and photons. The boron neutron capture therapy for deep tumors, except for epithermal neutrons, the greater the amount of rest of the radiation is, the greater the proportion of non-selective dose deposition in normal tissue is, so these radiation which will cause unnecessary doses should be minimized.

The International Atomic Energy Agency (IAEA) has given recommendations for the air beam quality factors for neutron sources for clinical boron neutron capture therapy. The recommendations can be used to differentiate the neutron sources and as reference for selecting neutron production pathways and designing the beam shaping assembly. Wherein, the recommendation for photon contamination: photon contamination $<2 \times 10^{-13}$ Gy-cm$^2$/n.

Photon contamination is also called gamma-ray contamination. The gamma ray belonging to long-range penetration radiation will non-selectively cause dose deposit of all tissues in beam path, so that lowering the quantity of gamma ray is also the exclusive requirement in the neutron source design. Gamma ray dose accompanied per unit epithermal neutron flux is defined as gamma ray contamination which is suggested being less than 2×10-13 Gy-cm2/n.

Note: the epithermal neutron energy range is between 0.5 eV and 40 keV, the thermal neutron energy range is lower than 0.5 eV, and the fast neutron energy range is higher than 40 keV.

In addition to the air beam quality factors, in order to better understand the neutron dose distribution in the human body, the human head tissue prosthesis is used for dose calculation in the embodiments of the present disclosure, and beam quality factors of the prosthesis are used as references for the design of the neutron beam, which will be described in detail below.

The dose distribution in the tissue is obtained using a prosthesis, and, the phantom beam quality factors are derived based on the dose-depth curves of the normal tissue and the tumor. The following two parameters can be used to compare the benefits of different neutron beam treatments.

1. Advantage Depth (AD)

Tumor dose is equal to the maximum dose of the normal tissue. At a position behind this depth, the dose received by the tumor cells is less than the maximum dose of the normal tissue, that is, the advantage of boron neutron capture is lost. The advantage depth represents the penetrability of the neutron beam, wherein the larger the advantage depth is, the larger the treatable tumor depth is, and the unit is cm.

2. Advantage Dose Rate (AR)

From the brain surface to the advantage depth, the average dose rate received by tumor and normal tissues is called the advantage dose rate. The calculation of average dose can be obtained by integrating the dose-depth curve. The greater the advantage dose rate is, the better the therapeutic effect of the neutron beam is.

In order to provide a comparative basis for the design of beam shaping assembly, the following parameters are used to evaluate the performance of neutron beam dose in the embodiments of the present disclosure:

1. 30.0 RBE-Gy treatable depth ≥7 cm;
2. AD≥10 cm;
3. AR≥5.5.

Note: RBE represents relative biological effectiveness. Because the biological effectiveness caused by photons and neutrons are different, the above dose should be respectively multiplied with the relative biological effectiveness of the different tissues to obtain the equivalent dose.

The present disclosure will be described in further detail with reference to the accompanying drawings. The beam shaping assembly 100 for neutron capture therapy as shown in FIG. 1 includes a neutron generating device 110, a moderator 120, a disturbing unit 130, a beam outlet 140, and a reflector 150. Wherein the neutron generating device 110 is classified into a nuclear reactor type neutron generating device and an accelerator type neutron generating device. Although the two types of neutron generating devices have different mechanisms for generating neutrons, a large number of strong penetrating gamma rays are accompanied in the process of neutron production. The neutrons generated by the neutron generating device converge into a neutron beam 160, and the center line of the neutron beam 160 is defined as a neutron axis X. Since the neutron beam 160 generated from the neutron generating device includes not only the epithermal neutrons required for the treatment, but also radiation such as fast neutrons, thermal neutrons, and gamma rays that cause damage to the patient, the neutron beam 160 needs to be filtered by the moderator 120. The function of the moderator 120 is to moderate the fast neutrons in the neutron beam 160 to an epithermal neutron energy region. During the process of moderating of the moderator 120, the neutrons will deviate from the onward direction of the neutron beam 160 and spread to the periphery, and the reflector 150 is used to reflect neutrons that diffuse around back to the neutron beam 160 to enhance the intensity of the neutron beam 160. The reflector 150 is mainly made of a substance having a strong neutron reflection ability such as lead or nickel. The disturbing unit 130 is located between the moderator 120 and the beam outlet 140, and the axis of the disturbing unit 130 is parallel or coincides with the neutron axis X. The material of the disturbing unit 130 is selected from the group consisting of rhenium, hafnium, lutetium, lead, cerium, zinc, bismuth, terbium, indium, antimony, gallium, lanthanum, tellurium, tin, selenium, yttrium, aluminum, strontium, barium, silicon, zirconium, rubidium, calcium, sulfur, iron, carbon, beryllium, magnesium, phosphorus, chromium, lithium, sodium, nickel element and combinations thereof. The disturbing unit 130 may be a cuboid, a cube, a sphere, a cylinder or an irregular shape of a small volume to satisfy the ability to reduce the gamma ray content in the neutron beam without significant negative impact to the quality of the neutron beam. The disturbing unit 130 in the beam shaping assembly 100 shown in FIG. 1 is a cylinder. The drawing of the cylinder is only for demonstrating the technical solutions of the present disclosure, and does not limit the technical solutions to be protected by the present disclosure. The neutron beam 160 passes through the disturbing unit 130, wherein the gamma rays are absorbed, reflected or scattered by the disturbing unit 130 to reduce the gamma ray content in the neutron beam 160. In addition, the gamma rays reflected or scattered by the disturbing unit 130 deviates from the neutron beam and irradiates onto the reflector 150, and the gamma rays undergo the Compton effect, the photoelectric effect or the electron pair effect under the action of the reflector 150 to be further attenuated, and the neutron beam 160 exits the beam shaping assembly 100 from the beam outlet 140 after the gamma rays are filtered.

Figure 3:
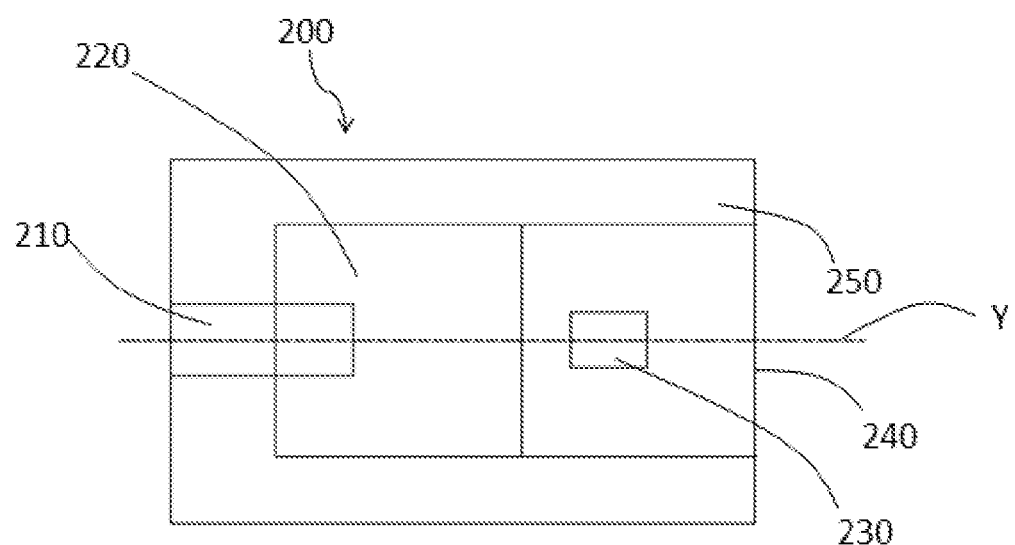
FIG. 3 is a schematic view of a beam shaping assembly with a cylindrical moderator.

FIG. 3 is a schematic view of a beam shaping assembly comprising a cylindrical moderator, which has the same principle in the process for neutron capture therapy as the beam shaping assembly comprising a diamond-shaped moderator shown in FIG. 1. The beam shaping assembly 200 comprises a neutron generating device 210, a moderator 220, a disturbing unit 230, a beam outlet 240, and a reflector 250. The center line of the neutron beam is defined as a neutron axis Y, wherein the moderator 220 is a cylinder. FIG. 3 is a schematic cross-sectional view of a cylindrical moderator.

Figure 2:
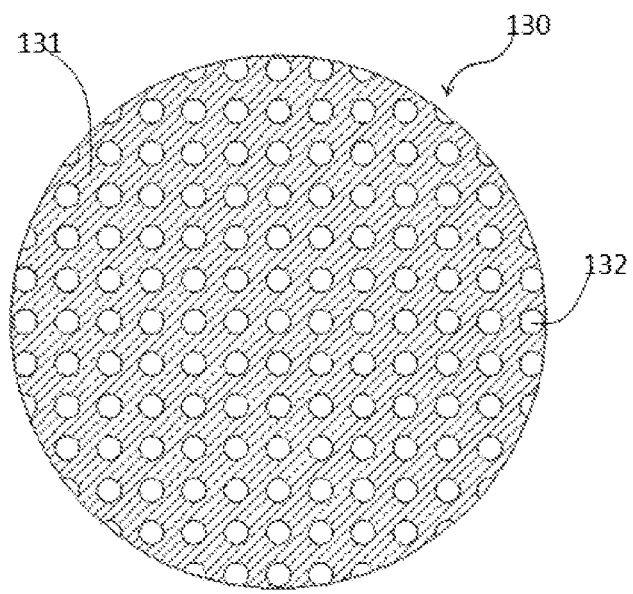
FIG. 2 is a cross-sectional view of a disturbing unit having a porous structure in a beam shaping assembly.

The attenuation of gamma rays is not only related to the material of the disturbing unit, but also related to the structure and shape of the disturbing unit. The disturbing units are classified into a disturbing unit with dense structure and a disturbing unit with porous structure according to the differences of the structures. Under normal circumstances, the shielding effect on the gamma ray of the disturbing unit with dense structure is better than that of the disturbing unit with porous structure. FIG. 2 is a schematic cross-sectional view of a cylindrical disturbing unit 130. The material 131 constituting the disturbing unit 130 is a complete whole with a plurality of pores 132 inside thereof. Although the disturbing unit with the porous structure is less effective at shielding gamma rays than the disturbing unit with the dense structure, it requires relatively few materials. In the economic sense, when there is not much requirement for the attenuation of gamma rays in the neutron beam, the disturbing unit with the porous structure not only satisfy the requirement of reducing the gamma ray content in the neutron beam, but also has no significant adverse influence on the quality of the neutron beam.

The beneficial effects of the technical solution of the present disclosure are further described below by way of embodiments.

Embodiment 1

The gamma ray attenuation and neutron beam quality in this present embodiment are calculated by MCNP software (which is a general-purpose software package for calculating neutrons, photons, charged particles or coupled neutron/photon/charged particle transport problems in three-dimensional complex geometries based on Monte Carlo method developed by the Los Alamos National Laboratory, US). Wherein, in this embodiment, the disturbing unit in the beam shaping assembly is a cylinder having a porous structure as shown in FIGS. 1 and 2 and the moderator in the beam shaping assembly is composed of 85% magnesium fluoride and 15% lithium fluoride. The moderator is a diamond shape as shown in FIG. 1. The diamond-shaped moderator is composed of a first cone portion and a second cone portion, and the first cone portion adjacent to the second cone portion, and the outer contours of the two cones are tilted in opposite directions as shown in FIG. 1. Wherein, the height of the cylindrical disturbing unit was 10 cm, the radius of the bottom circular surface was 5 cm, and the disturbing unit is located between the moderator and the beam outlet. The influence of the disturbing unit on the neutron beam quality and the shielding effect on the gamma rays under the above conditions are shown in Table 1.

TABLE 1

Influence of cylindrical disturbing unit with a radius of the bottom surface of 5 cm and a height of 10 cm on neutron beam quality and shielding effect on gamma rays

| Material of disturbing unit | Gamma ray content in neutron beam (Gy * cm$^2$/n) | Neutron beam quality | | 30 RBE-Gy treatable depth (cm) |
|---|---|---|---|---|
| | | Advantage depth (cm) | Advantage dose rate | |
| rhenium | 4.15 * 10$^{-14}$ | 10.82 | 5.67 | 7.35 |
| hafnium | 4.33 * 10$^{-14}$ | 10.79 | 5.66 | 7.34 |
| lutetium | 4.59 * 10$^{-14}$ | 10.83 | 5.65 | 7.33 |
| lead | 4.60 * 10$^{-14}$ | 10.79 | 5.69 | 7.40 |
| cerium | 4.79 * 10$^{-14}$ | 10.73 | 5.67 | 7.37 |
| zinc | 4.81 * 10$^{-14}$ | 10.76 | 5.69 | 7.42 |
| bismuth | 4.86 * 10$^{-14}$ | 10.80 | 5.67 | 7.40 |
| terbium | 5.03 * 10$^{-14}$ | 10.86 | 5.66 | 7.37 |
| indium | 5.24 * 10$^{-14}$ | 10.76 | 5.67 | 7.32 |
| antimony | 5.26 * 10$^{-14}$ | 10.78 | 5.67 | 7.38 |
| gallium | 5.29 * 10$^{-14}$ | 10.75 | 5.66 | 7.41 |
| lanthanum | 5.30 * 10$^{-14}$ | 10.76 | 5.66 | 7.37 |
| tellurium | 5.31 * 10$^{-14}$ | 10.72 | 5.66 | 7.37 |
| tin | 5.38 * 10$^{-14}$ | 10.80 | 5.67 | 7.42 |
| selenium | 5.41 * 10$^{-14}$ | 10.73 | 5.66 | 7.34 |
| yttrium | 5.78 * 10$^{-14}$ | 10.77 | 5.67 | 7.42 |
| aluminum | 6.36 * 10$^{-14}$ | 10.76 | 5.67 | 7.40 |
| strontium | 6.54 * 10$^{-14}$ | 10.82 | 5.64 | 7.37 |
| barium | 6.54 * 10$^{-14}$ | 10.74 | 5.65 | 7.35 |
| silicon | 6.73 * 10$^{-14}$ | 10.80 | 5.65 | 7.34 |
| zirconium | 6.78 * 10$^{-14}$ | 10.83 | 5.66 | 7.41 |
| rubidium | 7.06 * 10$^{-14}$ | 10.78 | 5.65 | 7.27 |
| calcium | 7.33 * 10$^{-14}$ | 10.73 | 5.63 | 7.26 |
| sulfur | 7.40 * 10$^{-14}$ | 10.75 | 5.64 | 7.31 |
| iron | 7.49 * 10$^{-14}$ | 10.75 | 5.65 | 7.36 |
| carbon | 7.59 * 10$^{-14}$ | 10.76 | 5.67 | 7.43 |
| beryllium | 7.71 * 10$^{-14}$ | 10.73 | 5.67 | 7.43 |
| magnesium | 7.81 * 10$^{-14}$ | 10.82 | 5.66 | 7.41 |
| phosphorus | 7.81 * 10$^{-14}$ | 10.70 | 5.66 | 7.35 |
| chromium | 8.15 * 10$^{-14}$ | 10.76 | 5.65 | 7.37 |
| lithium | 8.61 * 10$^{-14}$ | 10.79 | 5.62 | 7.30 |
| sodium | 8.69 * 10$^{-14}$ | 10.80 | 5.64 | 7.36 |
| nickel | 8.73 * 10$^{-14}$ | 10.69 | 5.66 | 7.43 |

The disturbing unit is not provided in the comparative example of the present example, and the remaining parameters of the comparative example is the same as those of the beam shaping assembly in the above embodiment. In the neutron beam of the comparative example, the gamma ray content is 8.78*10-14Gy*cm2/n, the advantage depth is 10.74 cm, the advantage dose rate is 5.61, and the treatment depth of 30RBE-Gy is 7.27 cm. By comparison, it is found that the disturbing units made of 33 kinds of single elements in the present embodiment had no obvious negative influence on the neutron beam quality of the beam shaping assembly, and the advantage depth (AD) values all are 10.74±0.12, the advantage dose rate (AR) values are 5.6±0.09, and the 30 RBE-Gy treatable depth are 7.3±0.13. And the gamma ray contents in the neutron beams were reduced to varying degrees.

Embodiment 2

In the present embodiment, the disturbing unit is a cylinder with a compact structure, wherein the radius of the bottom surface of the cylinder is 6 cm, and the height of the cylinder is 3 cm. The other conditions are the same as those in Embodiment 1. When lead, antimony, nickel, aluminum and carbon are used as the disturbing units respectively, the disturbing units on the neutron beam quality and shielding effect on gamma rays are calculated by MCNP software. The results are shown in Table 2:

TABLE 2

Influence of cylindrical disturbing unit with compact structure with a radius of the bottom surface of 6 cm and a height of 3 cm on the neutron beam quality and shielding effect on gamma rays of magnesium fluoride and lithium fluoride as moderator

| Material of disturbing unit | Gamma ray content in neutron beam (Gy * cm$^2$/n) | Neutron beam quality | | 30 RBE-Gy treatable depth |
|---|---|---|---|---|
| | | Advantage depth (cm) | Advantage dose rate | |
| lead | 5.58 * 10$^{-14}$ | 10.75 | 5.64 | 7.33 |
| bismuth | 6.03 * 10$^{-14}$ | 10.72 | 5.64 | 7.33 |
| nickel | 7.33 * 10$^{-14}$ | 10.73 | 5.64 | 7.33 |
| aluminum | 8.09 * 10$^{-14}$ | 10.74 | 5.63 | 7.33 |
| carbon | 8.36 * 10$^{-14}$ | 10.72 | 5.62 | 7.34 |

The principles of different materials used as disturbing units to shield gamma rays are the same. Therefore, in the present embodiment, only lead, antimony, nickel, aluminum and carbon are randomly selected as the disturbing unit to illustrate the technical effect of adding the disturbing unit in the beam shaping assembly, and the material constituting the disturbing unit is not limited to these substances. The comparative example in the present embodiment is the same as the comparative example in Embodiment 1, both the comparative example are not provided with the disturbing unit, and the remaining parameters are the same as those of the present embodiment. In the neutron beam of the comparative example, the gamma ray content is 8.78*10-14Gy*cm2/n, the advantage depth is 10.74 cm, the advantage dose rate was 5.61, and the 30 RBE-Gy treatable depth is 7.27 cm. By comparison, it can be seen that the solid disturbing unit can also have a better shielding effect on the gamma rays under the premise of improving the quality of the neutron beam.

Embodiment 3

In the present embodiment, the material of the moderator is aluminum fluoride, and the shape of the moderator is the diamond shape as Embodiment 1, and the disturbing unit is a cylinder with porous structure, wherein the size of the cylinder is the bottom radius is 6 cm and a height is 3 cm. The disturbing unit is located between the moderator and the beam outlet. Under the above conditions, when lead, antimony, aluminum and carbon are used as the disturbing units respectively, the disturbing unit on the neutron beam quality and shielding effect on gamma rays are calculated by MCNP software. The results are shown in Table 3:

TABLE 3

Influence of cylindrical disturbing unit with porous structure with a radius of the bottom surface of 6 cm and a height of 3 cm on the neutron beam quality and shielding effect on gamma rays of aluminum fluoride as moderator

| Material of disturbing unit | Gamma ray content in neutron beam (Gy * cm$^2$/n) | Neutron beam quality | | 30 RBE-Gy treatable depth |
|---|---|---|---|---|
| | | Advantage depth (cm) | Advantage dose rate | |
| lead | 6.31 * 10$^{-14}$ | 10.88 | 5.60 | 7.09 |
| bismuth | 6.68 * 10$^{-14}$ | 10.79 | 5.59 | 7.10 |
| aluminum | 8.75 * 10$^{-14}$ | 10.86 | 5.59 | 7.06 |
| carbon | 9.22 * 10$^{-14}$ | 10.79 | 5.59 | 7.16 |

The principles of different materials used as disturbing units to shield gamma rays are the same. Therefore, in the present embodiment, only lead, antimony, aluminum and carbon are randomly selected as the disturbing unit to illustrate the technical effect of adding the disturbing unit in the beam shaping assembly, and the material constituting the disturbing unit is not limited to these substances. The different experimental condition between the comparative example in the present embodiment and the Embodiment 3 is only that disturbing unit the comparative example in the present embodiment is not provided with the disturbing unit, and the other conditions is the same as those in the beam shaping assembly in Example 3. In the neutron beam of the comparative example, the gamma ray content is 11.9*10-14Gy*cm2/n, the advantage depth is 10.81 cm, the advantage dose rate is 5.54, and the 30 RBE-Gy treatable depth is 6.98 cm. It can be seen from Table 3 that the moderators with different materials has an influence on the neutron beam quality. The 30 RBE-Gy treatable depth in the present embodiment is lower than that in Embodiment 1 and Embodiment 2, and the reduction of the 30 RBE-Gy treatable depth is caused by the difference in the materials of the moderator. Comparing the comparative example of Example 3 with Example 3, it can be found that under the condition that the materials of the moderators is the same, the presence of the disturbing unit has an improved effect on the neutron beam quality, and the disturbing unit can effectively shield the gamma rays in the neutron beam.

Embodiment 4

In the present embodiment, Fluental is selected as the material of the moderator (Fluental is the moderating material mentioned in U.S. Pat. No. 5,703,918B), and the other parameters are the same as those in Embodiment 3. When lead, antimony, aluminum and carbon are used as the disturbing units respectively, the disturbing units on the neutron beam quality and shielding effect on gamma rays are calculated by MCNP software. The results are shown in Table 4:

TABLE 4

Influence of cylindrical disturbing unit with porous structure with a radius of the bottom surface of 6 cm and a height of 3 cm on the neutron beam quality and shielding effect on gamma rays of Fluental as moderator

| Material of disturbing unit | Gamma ray content in neutron beam (Gy * cm$^2$/n) | Neutron beam quality | | 30 RBE-Gy treatable depth |
|---|---|---|---|---|
| | | Advantage depth (cm) | Advantage dose rate | |
| lead | 4.85 * 10$^{-14}$ | 10.88 | 5.55 | 6.77 |
| bismuth | 5.17 * 10$^{-14}$ | 10.91 | 5.54 | 6.79 |

TABLE 4-continued

Influence of cylindrical disturbing unit with porous structure with a radius of the bottom surface of 6 cm and a height of 3 cm on the neutron beam quality and shielding effect on gamma rays of Fluental as moderator

| Material of disturbing unit | Gamma ray content in neutron beam (Gy * cm$^2$/n) | Neutron beam quality | | 30 RBE-Gy treatable depth |
|---|---|---|---|---|
| | | Advantage depth (cm) | Advantage dose rate | |
| aluminum | 6.81 * 10$^{-14}$ | 10.89 | 5.54 | 6.80 |
| carbon | 6.83 * 10$^{-14}$ | 10.85 | 5.57 | 6.89 |

The principles of different materials used as disturbing units to shield gamma rays are the same. Therefore, in the present embodiment, only lead, antimony, aluminum and carbon are randomly selected as the disturbing unit to illustrate the technical effect of adding the disturbing unit in the beam shaping assembly, and the material constituting the disturbing unit is not limited to these substances. The beam shaping assembly of the present embodiment is not provided with the disturbing unit as a comparative example. In the neutron beam of the comparative example, the gamma ray content is 9.25*10-14, the advantage depth is 10.86 cm, the advantage dose rate is 5.47, and the 30 RBE-Gy treatable depth is 6.67 cm. Comparing the neutron beam quality of the present embodiment with those of embodiment 1 to 3, the 30 RBE-Gy treatable depth are reduced to varying degrees due to the use of moderators with different materials. However, by comparison of Embodiment 4 with the comparative example, it can be concluded that due to the presence of the disturbing units, the gamma ray content in the neutron beam is significantly reduced and the 30 RBE-Gy treatable depth of the neutron beam quality is increased.

Embodiment 5

In the present embodiment, 85% magnesium fluoride and 15% lithium fluoride are selected as the moderator material, wherein the shape of the moderator is a cylinder. FIG. 3 is a cross-sectional view showing the beam shaping assembly in the present embodiment. The disturbing unit is a porous cylinder, and is located between the moderator and the beam outlet, wherein the height of the cylindrical disturbing unit is 10 cm, and the radius of the bottom circular surface is 5 cm. The effect of the disturbing unit on the neutron beam quality and the shielding effect on the gamma rays under the above conditions are shown in Table 5:

TABLE 5

Influence of the disturbing unit on the neutron beam generated by the cylindrical moderator and shielding effect on the gamma rays in the beam shaping assembly

| Material of disturbing unit | Gamma ray content in neutron beam (Gy * cm$^2$/n) | Neutron beam quality | | 30 RBE-Gy treatable depth |
|---|---|---|---|---|
| | | Advantage depth (cm) | Advantage dose rate | |
| rhenium | 2.59 * 10$^{-14}$ | 13.24 | 5.64 | 9.43 |
| lead | 2.99 * 10$^{-14}$ | 13.15 | 5.63 | 9.35 |
| bismuth | 3.04 * 10$^{-14}$ | 13.10 | 5.64 | 9.30 |
| aluminum | 5.64 * 10$^{-14}$ | 12.91 | 5.63 | 9.12 |
| carbon | 6.06 * 10$^{-14}$ | 13.22 | 5.66 | 9.35 |

The principles of different materials used as disturbing units to shield gamma rays are the same. Therefore, in the present example, only rhenium, lead, bismuth, aluminum and carbon are randomly selected as the disturbing unit to illustrate the technical effect of adding the disturbing unit in the beam shaping assembly, and the material constituting the disturbing unit is not limited to these substances. The beam shaping assembly of the present embodiment without the disturbing unit is used as a comparative example. In the neutron beam of the comparative example, the gamma ray content is 6.47*10-14, the advantage depth is 12.82 cm, the advantage dose rate is 5.58, and the 30 RBE-Gy treatable depth y is 8.76 cm. It can be seen from the comparison between Embodiment 5 and the corresponding comparative example that the neutron beam quality of the neutron beam at the beam outlet of the beam shaping assembly where the disturbing units made of different materials is located has different degrees of improvement disturbing unit, for example, the advantage depth and the 30 RBE-Gy treatable depth are increased to different extents compared with the comparative example, which are beneficial to the treatment effect. Moreover, the gamma ray contents in the neutron beam are reduced to different extents compared with the comparative example. Since the moderator used in the present embodiment is a cylinder, it is further explained that regardless of the shape of the moderator in the beam shaping assembly, the presence of the disturbing unit can effectively reduce the gamma ray content in the neutron beam under the premise that the quality of the neutron beam is not significantly adversely affected.

It can be found from Embodiment 1 and 2 that whether the internal structure of the disturbing unit is a porous structure or a compact structure, the disturbing unit has a shielding effect on the gamma rays in the neutron beam. It can be found from the comparison of Embodiments 1, 3 and 4 that under the condition that the other parameters are the same, the moderators of different materials has influence on the neutron beam quality, under the condition that the materials of the moderators are the same, the presence of the disturbing unit can significantly reduce the gamma ray content in the neutron beam, thereby further illustrating the improvement effect of the disturbing unit on the quality of the neutron beam.

The beam shaping bodies in Embodiments 1 to 5 are all cylinders, and the height of the cylinders as the beam shaping assembly are 80 to 100 cm, and the radii of the bottom surfaces of the cylinders are 60 to 70 cm. It can be concluded from Embodiments 1 to 5 that the nature of the disturbing unit to reduce the gamma ray content in the neutron beam without any significant negative effect on the quality of the neutron beam is substantially unaffected by factors other than the disturbing unit. In the technical solution provided by the present disclosure, regardless of the size of the disturbing unit relative to the beam shaping assembly, the presence of the disturbing unit can reduce the content of the gamma ray in the neutron beam. However, it should be noted that in the same beam shaping assembly, the larger the size of the disturbing unit is, the greater the influence of the disturbing unit on the neutron beam quality is, accordingly, the smaller the size of the disturbing unit is, although the smaller the influence of the disturbing unit on the neutron beam quality is, the attenuation of the gamma ray in the neutron beam is also reduced accordingly.

The shielding effect of the disturbing unit on the gamma rays in the neutron beam is mainly by the absorption or reflection of the gamma rays by the material constituting the disturbing unit. The gamma rays in the neutron beam will have a certain degree of attenuation as long as it passes through the disturbing unit. Whether the disturbing unit can reduce the gamma ray content in the neutron beam is not depend on the shape and size of the disturbing unit and the position of the disturbing unit in the beam shaping assembly.

The beam shaping assembly for neutron capture therapy disclosed in the present disclosure is not limited to the contents described in the above embodiments and the structure represented by the drawings. Obvious modifications, substitutions or alterations of the materials, shapes and positions of the components in the present disclosure are intended to be within the scope of the present disclosure.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A beam shaping assembly for neutron capture therapy, comprising:
    a neutron generating device housed within the beam shaping assembly for generating neutrons;
    a beam outlet, wherein the neutrons form a neutron beam in a direction from the neutron generating device to the beam outlet, and the neutron beam defines a beam axis;
    a moderator adjacent to the neutron generating device for moderating fast neutrons in the neutron beam to epithermal neutrons; and
    a disturbing unit being a cylinder, wherein the radius of the bottom surface of the cylinder is 5 to 6 cm, and the height of the cylinder is 3 to 5 cm;
    wherein the beam shaping assembly produces gamma rays in a process of adjusting an energy spectrum of the neutron beam, the disturbing unit is located between the moderator and the beam outlet for allowing the neutron beam to pass through the disturbing unit and reducing contents of the gamma rays in the neutron beam passing through the beam outlet.

2. The beam shaping assembly for neutron capture therapy according to claim 1, wherein a material of the disturbing unit is selected from the group consisting of rhenium, hafnium, lutetium, lead, cerium, zinc, bismuth, terbium, indium, antimony, gallium, lanthanum, tellurium, tin, selenium, yttrium, aluminum, strontium, barium, silicon, zirconium, rubidium, calcium, sulfur, iron, carbon, beryllium, magnesium, phosphorus, chromium, lithium, sodium, nickel element and combinations thereof.

3. The beam shaping assembly for neutron capture therapy according to claim 2, wherein the disturbing unit consists of any single element of rhenium, hafnium, lutetium, lead, cerium, zinc, bismuth, terbium, indium or antimony, and a proportion of gamma rays in the neutron beam is reduced by at least 30%.

4. The beam shaping assembly for neutron capture therapy according to claim 2, wherein in a phantom beam quality of the neutron beam passing through the disturbing unit, an advantage depth is ≥10.69 cm.

5. The beam shaping assembly for neutron capture therapy according to claim 1, wherein an internal structure of the disturbing unit is a dense structure or a porous structure.

6. The beam shaping assembly for neutron capture therapy according to claim 1, wherein the beam shaping assembly further includes a reflector surrounding the moderator and the disturbing unit for reflecting neutrons deviating from the neutron beam back to the neutron beam to enhance an intensity of the neutron beam, and wherein the reflector is made of a material having a strong neutron reflection ability.

7. The beam shaping assembly for neutron capture therapy according to claim 6, wherein when the neutron beam containing the gamma rays passes through the disturbing unit, the disturbing unit reduces the contents of the gamma rays in the neutron beam by absorbing the gamma rays through photoelectric effect, scattering the gamma rays through Compton effect, or converting the gamma rays into positive and negative electron pairs through electron pair effect, respectively, and the gamma rays scattered by the disturbing unit are further attenuated by reabsorption or reflection after encountering the reflector.

8. The beam shaping assembly for neutron capture therapy according to claim 1, wherein the cylinder defines an axis and the axis of the cylinder coincides or is parallel to the beam axis.

9. The beam shaping assembly for neutron capture therapy according to claim 1, wherein an energy range of the fast neutrons is higher than 40 keV and an energy range of the epithermal neutrons is between 0.5 eV and 40 keV.

10. A beam shaping assembly for neutron capture therapy, comprising:
   a neutron generating device housed within the beam shaping assembly for generating neutrons;
   a beam outlet, wherein the neutrons form a neutron beam in a direction from the neutron generating device to the beam outlet, and the neutron beam defines a beam axis;
   a moderator adjacent to the neutron generating device for moderating fast neutrons in the neutron beam to epithermal neutrons;
   a disturbing unit, wherein an internal structure of the disturbing unit is a porous structure; and
   a reflector surrounding the moderator and the disturbing unit for reflecting neutrons deviating from the neutron beam back to the neutron beam to enhance the neutron beam intensity;
   wherein the beam shaping assembly produces gamma rays in a process of adjusting an energy spectrum of the neutron beam, the disturbing unit is located after the neutron generating device for allowing the neutron beam to pass through the disturbing unit and reducing contents of the gamma rays in the neutron beam passing through the beam outlet.

11. The beam shaping assembly for neutron capture therapy according to claim 10, wherein a material of the disturbing unit is selected from the group consisting of rhenium, hafnium, lutetium, lead, cerium, zinc, bismuth, terbium, indium, antimony, gallium, lanthanum, tellurium, tin, selenium, yttrium, aluminum, strontium, barium, silicon, zirconium, rubidium, calcium, sulfur, iron, carbon, beryllium, magnesium, phosphorus, chromium, lithium, sodium, nickel element and combinations thereof.

12. The beam shaping assembly for neutron capture therapy according to claim 10, wherein when the neutron beam containing the gamma rays passes through the disturbing unit, the disturbing unit reduces the contents of the gamma rays in the neutron beam by absorbing the gamma rays through photoelectric effect, scattering the gamma rays through Compton effect, or converting the gamma rays into positive and negative electron pairs through electron pair effect, respectively, and the gamma rays scattered by the disturbing unit are further attenuated by reabsorption or reflection after encountering the reflector.

13. The beam shaping assembly for neutron capture therapy according to claim 10, wherein the disturbing unit is a cylinder defining an axis and the axis of the cylinder coincides or is parallel to the beam axis.

14. A beam shaping assembly for neutron capture therapy, comprising:
   a neutron generating device housed within the beam shaping assembly for generating neutrons;
   a beam outlet, wherein the neutrons form a neutron beam in a direction from the neutron generating device to the beam outlet, and the neutron beam defines a beam axis;
   a moderator adjacent to the neutron generating device for moderating fast neutrons in the neutron beam to epithermal neutrons; and
   a disturbing unit;
   wherein the beam shaping assembly produces gamma rays in a process of adjusting an energy spectrum of the neutron beam, the disturbing unit defines an axis and the axis of the disturbing unit coincides or is parallel to the beam axis for allowing the neutron beam to pass through the disturbing unit and reducing contents of the gamma rays in the neutron beam passing through the beam outlet, and an internal structure of the disturbing unit is a porous structure.

15. The beam shaping assembly for neutron capture therapy according to claim 14, wherein a material of the disturbing unit is selected from the group consisting of rhenium, hafnium, lutetium, lead, cerium, zinc, bismuth, terbium, indium, antimony, gallium, lanthanum, tellurium, tin, selenium, yttrium, aluminum, strontium, barium, silicon, zirconium, rubidium, calcium, sulfur, iron, carbon, beryllium, magnesium, phosphorus, chromium, lithium, sodium, nickel element and combinations thereof.

16. The beam shaping assembly for neutron capture therapy according to claim 14, wherein the beam shaping assembly further includes a reflector surrounding the moderator and the disturbing unit for reflecting neutrons deviating from the neutron beam back to the neutron beam to enhance an intensity of the neutron beam, and wherein the reflector is made of a material having a strong neutron reflection ability.

17. The beam shaping assembly for neutron capture therapy according to claim 16, wherein when the neutron beam containing the gamma rays passes through the disturbing unit, the disturbing unit reduces the contents of the gamma rays in the neutron beam by absorbing the gamma rays through photoelectric effect, scattering the gamma rays through Compton effect, or converting the gamma rays into positive and negative electron pairs through electron pair effect, respectively, and the gamma rays scattered by the disturbing unit are further attenuated by reabsorption or reflection after encountering the reflector.

18. The beam shaping assembly for neutron capture therapy according to claim 14, wherein the disturbing unit is a cylinder, the radius of the bottom surface of the cylinder is 5 to 6 cm, and the height of the cylinder is 3 to 5 cm.

* * * * *